(12) United States Patent
Yamamoto et al.

(10) Patent No.: US 6,949,634 B2
(45) Date of Patent: Sep. 27, 2005

(54) METHOD FOR SYNTHESIZING CDNA

(75) Inventors: Junko Yamamoto, Otsu (JP); Kazue Miyake, Uji (JP); Hiroyuki Mukai, Moriyama (JP); Fumitsugu Hino, Kusatsu (JP); Ikunoshin Kato, Uji (JP)

(73) Assignee: Takara Shuzo Co., Ltd., Kyoto (JP)

( * ) Notice: Subject to any disclaimer, the term of this patent is extended or adjusted under 35 U.S.C. 154(b) by 121 days.

(21) Appl. No.: 10/201,314

(22) Filed: Jul. 24, 2002

(65) Prior Publication Data

US 2003/0077762 A1 Apr. 24, 2003

Related U.S. Application Data

(62) Division of application No. 09/856,539, filed as application No. PCT/JP99/06560 on May 23, 2001, now Pat. No. 6,485,917.

(51) Int. Cl.$^7$ .......................... C07H 19/00; C12P 19/34; C12N 9/00
(52) U.S. Cl. .................. 536/22.1; 435/91.2; 435/91.21; 435/183
(58) Field of Search .............................. 536/22.1, 23.2; 435/183, 91.21, 91.2

(56) References Cited

U.S. PATENT DOCUMENTS

| | | | |
|---|---|---|---|
| 5,407,800 A | * 4/1995 | Gelfand et al. | 435/6 |
| 5,618,703 A | 4/1997 | Gelfand et al. | |
| 5,624,833 A | 4/1997 | Gelfand et al. | |
| 5,830,714 A | * 11/1998 | Swaminathan et al. | 435/91.2 |
| 6,406,891 B1 | * 6/2002 | Legerski | 435/91.1 |
| 6,410,277 B1 | * 6/2002 | Barnes | 435/91.2 |

FOREIGN PATENT DOCUMENTS

| | | |
|---|---|---|
| EP | 0 878 553 A2 | 11/1998 |
| EP | 0 921 196 A1 | 6/1999 |
| JP | 10-136998 | 5/1998 |
| WO | WO 97/39113 | 10/1997 |

OTHER PUBLICATIONS

Cline et al. PCR fidelity of Pfu DNA Polymerase and other thermostable DNA Polymerases, Nuclear Acids Res., vol. 24, No. 18, pp. 3546–3551, 1996 Stratagene Catalog. Gene Characterization kits. Stratagene Catalog, p. 39, 1988.*

Lu et al, "Construction and quality of complementary DNA libraries prepared from cytoplasmic RNA not enriched in pollyadenine positive DNA", Biological Abstracts No. 87058715; Gene (1988), vol. 71, No. 1, pp. 157–164.

Mallet et al; "Continuous RT–PCR Using AMV–RT and Taq DNA Polymerase: Characterization and Comparison to Uncoupled Procedures"; Bio Techniques (1995), vol. 18, No. 4, pp. 678–687.

Murakami, Y.; "Protein", Nucleic Acid and Enzyme (Japanese), 1996, vol. 41, No. 5, pp. 595–602.

Kawakami et al; "Cell Technology" (Japanese); 1997, vol. 16, No. 5, pp. 725–732.

Boehringer Mannheim 1997 Biochemicals Catalog, pp. 146–147, 150–153 and An Instruction Manual from Titan™ RT–PCR System, Cat. No. 1855476.

Catalogue Clonlech, Innovative Tools to Accelerate Discovery, 30:179 (1996).

* cited by examiner

Primary Examiner—Jehanne Sitton
Assistant Examiner—Suryaprabha Chunduru
(74) Attorney, Agent, or Firm—Browdy and Neimark, PLLC

(57) ABSTRACT

A method for synthesizing cDNA characterized by performing a reverse transcription reaction in the presence of an enzyme having a reverse transcriptional activity and another enzyme different from the former one which as a 3'-5' exonuclease activity.

8 Claims, No Drawings

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial
<220> FEATURE:
<223> OTHER INFORMATION: Designed oligonucleotide primer designated as
      Primer 1 to amplify transferrin receptor mRNA.

<400> SEQUENCE: 1
caagctagat cagcattctc                                              20

<210> SEQ ID NO 2
<211> LENGTH: 20
<212> TYPE: DNA
<213> ORGANISM: Artificial
<220> FEATURE:
<223> OTHER INFORMATION: Designed oligonucleotide primer designated as
      Primer 2 to amplify transferrin receptor mRNA.

<400> SEQUENCE: 2
gagactgtga gtagtgacac                                              20

<210> SEQ ID NO 3
<211> LENGTH: 20
<212> TYPE: DNA
<213> ORGANISM: Artificial
<220> FEATURE:
<223> OTHER INFORMATION: Designed oligonucleotide primer designated as
      Primer 3 to amplify transferrin receptor mRNA.

<400> SEQUENCE: 3
ccatcccatc atcttggtac                                              20

<210> SEQ ID NO 4
<211> LENGTH: 33
<212> TYPE: DNA
<213> ORGANISM: Artificial
<220> FEATURE:
<223> OTHER INFORMATION: Designed oligonucleotide primer designated as
      lacIOZalpha-F to am plify lacIOZ-alpha region of E. coli.

<400> SEQUENCE: 4
catagcgaat tcgcaaaacc tttcgcggta tgg                               33

<210> SEQ ID NO 5
<211> LENGTH: 33
<212> TYPE: DNA
<213> ORGANISM: Artificial
```

```
-continued

<220> FEATURE:
<223> OTHER INFORMATION: Designed oligonucleotide primer designated as
      lacIOZ-alpha-R to a mplify lacIOZ-alpha region of E. coli.

<400> SEQUENCE: 5
actacggaat tccacggaaa atgccgctca tcc                                    33
```

METHOD FOR SYNTHESIZING CDNA

This is a division of parent application Ser. No. 09/856,539, filed May 23, 2001 now U.S. Pat. No. 6,485,917 which is a 371 national stage application of International application PCT/JP99/06560, filed Nov. 25, 1999, which designated the United States and which application was not published in the English language.

TECHNICAL FIELD

The present invention relates to a novel method for synthesizing a cDNA and a kit used for the method, which are useful in a field of genetic engineering.

BACKGROUND ART

Analysis of mRNA molecules derived from various genes is very important in order to elucidate biological phenomena. Discovery of an RNA-dependent DNA polymerase, so-called a reverse transcriptase, from a retrovirus has enabled a reverse transcription reaction in which a cDNA is synthesized using an RNA as a template. As a result, methods for analyzing mRNA molecules have made rapid progress. Then, the methods for analyzing mRNA molecules using a reverse transcriptase have now become indispensable experimental methods for studying genes. Furthermore, these methods, which have been applied to cloning techniques and PCR techniques, have become indispensable techniques not only for studying genes but also in wide variety of fields including biology, medicine and agriculture.

However, the conventional reverse transcription methods had many problems such as interruption of a cDNA synthesis reaction, inability to synthesize a long cDNA, low fidelity, and damage of a template RNA in the course of reaction due to long time required for the reaction.

It is considered that the interruption of the cDNA synthesis reaction is due to the secondary structure formed by the RNA as a template. Optimal reaction temperature for a reverse transcriptase from a retrovirus is low. RNAs form complicated secondary structures during the reaction at the temperature. Then, the cDNA synthesis reaction is interrupted at the sites of such secondary structures. A method in which a heat-resistant reverse transcriptase is used has been proposed in order to solve the above-mentioned problem. However, the reactivity of this method is not satisfactory. In addition, reverse transcriptases have not been known to exhibit a proofreading activity during a reverse transcription reaction, and a method for synthesizing a cDNA with high fidelity has not been known.

As described above, it was difficult to synthesize a cDNA with high efficiency and with high fidelity according to the conventional methods. Thus, a more efficient method for synthesizing a cDNA has been desired.

OBJECTS OF INVENTION

The present invention has been made in view of the prior art as described above. The main object of the present invention is to solve the problems associated with the prior art and to provide a method for synthesizing a cDNA with high reaction efficiency and accuracy.

SUMMARY OF INVENTION

The present invention is outlined as follows. The first aspect of the present invention relates to a method for synthesizing a cDNA, characterized in that the method comprises conducting a reverse transcription reaction in the presence of an enzyme having a reverse transcription activity and another enzyme having a 3'-5' exonuclease activity.

The second aspect of the present invention relates to a method for amplifying a cDNA, characterized in that the method comprises conducting a gene amplification reaction using a cDNA synthesized according to the method of the first aspect as a template.

The third aspect of the present invention relates to a kit for cDNA synthesis, which contains an enzyme having a reverse transcription activity and another enzyme having a 3'-5' exonuclease activity.

The fourth aspect of the present invention relates to a kit for amplifying a cDNA by conducting a gene amplification reaction using a cDNA synthesized according to the method of the first aspect as a template, which contains an enzyme having a reverse transcription activity and another enzyme having a 3'-5' exonuclease activity as well as a reagent for the gene amplification reaction.

The present inventors have found the efficiency of cDNA synthesis and the fidelity are increased by conducting a reverse transcription reaction in the presence of an enzyme having a 3'-5' exonuclease activity in a cDNA synthesis reaction. Thus, the present invention has been completed.

DETAILED DESCRIPTION OF THE INVENTION

One of the main features of the method for synthesizing a cDNA of the present invention is that a cDNA is synthesized using an RNA as a template in a reverse transcription reaction system containing an enzyme having a 3'-5' exonuclease activity.

Examples of the samples containing RNAs which can be used in the method of the present invention include, but are not limited to, samples from organisms such as a cell, a tissue and a blood, and samples that may contain an organism such as a food, a soil and a waste water. The sample may be a preparation containing a nucleic acid obtained by processing the above-mentioned sample according to a known method. Examples of the preparations that can be used in the present invention include a cell destruction product or a sample obtained by fractionating the product, the total RNA in the sample, or a sample in which specific RNA molecules such as mRNAs are enriched.

The RNAs to which the method of the present invention can be applied include, but are not limited to, RNA molecules such as total RNA, mRNA, tRNA and rRNA in a sample, as well as specific RNA molecules (e.g., RNA molecules each having a common base sequence motif, transcripts obtained using an RNA polymerase and RNA molecules concentrated by a subtraction method). Any RNAs for which a primer used for a reverse transcription reaction can be prepared may be used.

The primer used for synthesizing a cDNA from an RNA as a template in the present invention is not limited to specific one as long as it is an oligonucleotide that has a nucleotide sequence complementary to that of the template RNA and that can anneal to the template RNA under reaction conditions used. The primer may be an oligonucleotide such as an oligo(dT) or an oligonucleotide having a random sequence (a random primer).

In view of specific annealing, the length of the primer is preferably 6 nucleotides or more, more preferably 10 nucleotides or more. In view of oligonucleotide synthesis, the length is preferably 100 nucleotides or less, more preferably 30 nucleotides or less. The oligonucleotide can be synthesized using, for example, the DNA synthesizer type 394 from Applied Biosystems Inc. (ABI) according to a phosphoramidite method. Alternatively, any methods including a phosphate triester method, an H-phosphonate method and a thiophosphonate method may be used to synthesize the oligonucleotide. The oligonucleotide may be derived from a biological sample. For example, it may be isolated and prepared from a DNA prepared from a natural sample digested with a restriction endonuclease. In view of synthesis of a cDNA from a template RNA, the concentration of the primer in the reverse transcription reaction mixture is preferably 0.1 µM or more, more preferably 0.5 µM or more. In view of inhibition of the reaction, the concentration is preferably 10 µM or less, more preferably 5 µM or less.

Any enzymes having reverse transcription activities can be used in the present invention as long as they have activities of synthesizing cDNAs using RNAs as templates. However, enzymes having reverse transcription activities at a high temperature (i.e., heat-resistant reverse transcriptases) are preferable for the purpose of the present invention. Examples of such enzymes which can be used include a DNA polymerase from a bacterium of genus *Thermus* (e.g., Tth DNA polymerase) and a DNA polymerase from a thermophilic bacterium of genus *Bacillus*. The presence of a manganese ion in a reaction mixture is indispensable for the exertion of the reverse transcription activity of Tth DNA polymerase. The manganese ion is known to reduce the fidelity of a PCR. Thus, it is required to eliminate the manganese ion when a reverse transcription reaction mixture in which Tth DNA polymerase is used is used for a PCR. DNA polymerases from thermophilic bacteria of genus *Bacillus* do not require the addition of a manganese ion for the exertion of its reverse transcription activity and the removal thereof upon a PCR. In this regard, DNA polymerases from thermophilic bacteria of genus *Bacillus* are preferable for the present invention. A DNA polymerase from *Bacillus caldotenax* (hereinafter referred to as Bca DNA polymerase) and a DNA polymerase from *Bacillus stearothermophilus* (hereinafter referred to as Bst DNA polymerase) are preferable. These enzymes do not require a manganese ion for the reactions. Furthermore, they can be used to synthesize a cDNA while suppressing the formation of secondary structure of the template RNA under high temperature conditions.

*Bacillus caldotenax* is a thermophilic bacterium having an optimal growth temperature of about 70° C. Bca DNA polymerase from this bacterium is known to have a DNA-dependent DNA polymerase activity, an RNA-dependent DNA polymerase activity (a reverse transcription activity), a 5'-3' exonuclease activity and a 3'-5' exonuclease activity.

The enzyme may be either an enzyme purified from its original source or a recombinant protein produced by using genetic engineering techniques. The enzyme may be subjected to modification such as substitution, deletion, addition or insertion by genetic engineering techniques or other means. Examples of such modified enzymes include Bca-BEST DNA polymerase (Takara Shuzo), which is Bca DNA polymerase lacking its 5'-3' exonuclease activity, and Bst DNA polymerase, Large fragment (New England Biolabs), which is Bst DNA polymerase lacking its 5'-3' exonuclease activity. The above-mentioned enzymes lacking their 5'-3' exonuclease activities can be preferably used in the present invention in particular.

The amount of the enzyme having a reverse transcription activity to be used is not specifically limited. The enzyme may be used, for example, in an amount used in a conventional reverse transcription reaction. The amount of the enzyme having a reverse transcription activity may be increased as compared with that for a conventional method to conduct the cDNA synthesis reaction more efficiently and to shorten the reaction time. For example, when BcaBEST DNA polymerase is used for conducting a reverse transcription reaction in a reaction volume of 20 µl, the amount of the enzyme in the reaction mixture is 0.5 U or more. In view of cDNA synthesis efficiency, it is preferably 22 U or more, more preferably 42 U or more. The activity of a DNA polymerase as described herein is based on the indication for a commercially available enzyme. An activity of incorporating 10 nmol of total nucleotides into an acid-insoluble precipitate in 3 minutes under reaction conditions suitable for the DNA polymerase is defined as 1 U. A DNA as a template and a reaction temperature suitable for each DNA polymerase are used. For example, in the case of BcaBEST DNA polymerase, an activity of incorporating 10 nmol of total nucleotides into an acid-insoluble precipitate in 30 minutes at 60° C. using polydeoxy (ATP-TTP) as a template/primer is defined as 1 U.

The method for synthesizing a cDNA of the present invention is characterized in that it comprises conducting a reverse transcription reaction in the presence of an enzyme having a 3'-5' exonuclease activity. The enzyme having a 3'-5' exonuclease activity to be used in the present invention is not limited to specific one as long as it has the activity. For example, a DNA polymerase having a 3'-5' exonuclease can be used. Examples of such enzymes include α-type DNA polymerases such as a DNA polymerase from a bacterium of genus *Pyrococcus* (Pfu DNA polymerase (Stratagene), Pyrobest DNA polymerase (Takara Shuzo), Deep Vent DNA polymerase (New England Biolabs), KOD DNA polymerase (Toyobo), Pwo DNA polymerase (Boehringer), etc.) and a DNA polymerase from a bacterium of genus *Thermococcus* (Vent DNA polymerase (New England Biolabs), etc.), and pol I-type DNA polymerases such as a DNA polymerase from *Escherichia coli* (polymerase I, Klenow fragment, etc.) and a DNA polymerase from a bacteriophage (T4 DNA polymerase, etc.). Preferably, an α-type DNA polymerase which exhibits a strong 3'-5' exonuclease activity is used. The pol I-type DNA polymerase or the α-type DNA polymerase refers to a series of enzymes classified on the basis of the amino acid sequence homology. The features of the amino acid sequences are described in Nucleic Acids Research, 15:4045–4657 (1991).

For the purpose of the present invention, an enzyme that acts on a 3'-terminus of a DNA hybridized with an RNA is used. Furthermore, an enzyme that exhibits a 3'-5' exonuclease activity at a high temperature is preferable. In this regard, an α-type DNA polymerase derived from a hyperthermophilic archaebacterium is preferable. The α-type type DNA polymerase derived from a hyperthermophilic archaebacterium is exemplified by a DNA polymerase from a bacterium of genus *Pyrococcus*.

A cDNA can be amplified by conducting a nucleic acid amplification reaction using the cDNA obtained according to the method described above as a template. Although it is not intended to limit the present invention, for example, a polymerase chain reaction (PCR) is used as the nucleic acid amplification reaction. The enzyme to be used for the PCR is not limited to specific one. A DNA polymerase conventionally used for a PCR can be used. The cDNA obtained according to the method as described above is synthesized from the template RNA with high fidelity. It is desired to conduct the PCR with high fidelity in order to reproduce the sequence from the RNA as accurately as possible. Thus, a DNA polymerase having high fidelity such as an α-type DNA polymerase from a thermophilic archaebacterium is preferably used for the cDNA amplification of the present invention. When a heat-resistant DNA polymerase having a 3'-5' exonuclease activity (e.g., an α-type DNA polymerase from a thermophilic archaebacterium) is used in the cDNA synthesis step, the same enzyme can be also used in the PCR step. Fidelity of a cDNA synthesis/amplification reaction can be determined according to a modification of the method of J. Cline et al. (J. Cline et al., Nucleic Acids Research, 24:3546–3551 (1996)).

The enzyme may be either an enzyme purified from its original source or a recombinant protein produced by using genetic engineering techniques. The enzyme may be subjected to modification such as substitution, deletion, addition or insertion by genetic engineering techniques or other means. A DNA polymerase having a 3'-5' exonuclease activity exhibits a proofreading activity which is effective in eliminating a base erroneously incorporated in a synthesized cDNA even if an RNA is used as a template. Thus, it can be used to synthesize a cDNA with high fidelity. In view of cDNA synthesis efficiency, the amount of the enzyme (in terms of polymerase activity) to be used in a reaction volume of 20 μl is preferably 1 U or less, more preferably 0.5 U or less. In view of the proofreading activity, the amount is preferably 0.01 U or more, more preferably 0.02 U or more.

By using the method of the present invention, the amount of synthesized cDNA can be increased, a longer cDNA can be synthesized, and a cDNA can be synthesized with higher fidelity as compared with the conventional reverse transcription methods. Furthermore, by combining the method of the present invention with related techniques such as cloning techniques and PCR techniques, it is possible to prepare a cDNA library or to conduct an RT-PCR more efficiently as compared with conventional methods, thereby allowing more accurate analysis of an mRNA of which the analysis by a conventional method was difficult due to the low expression level.

The kit for cDNA synthesis of the present invention is a kit to be used for the method for synthesizing a cDNA as described above. It is a kit for synthesizing a cDNA with high fidelity and with high efficiency. The kit is exemplified by one that contains the enzyme having a reverse transcription activity and the enzyme having a 3'-5' exonuclease activity as described above. The kit may contain a reaction buffer to be used for cDNA synthesis reaction using the enzyme described above, nucleotides and other reagents. cDNA can be synthesized efficiently, with high fidelity and readily by using such a kit.

The kit for amplifying a cDNA of the present invention is a kit to be used for the method for amplifying a cDNA as described above. It is a kit for amplifying a cDNA with high fidelity and with high efficiency. The kit is exemplified by one that contains the enzyme having a reverse transcription activity and the enzyme having a 3'-5' exonuclease activity as described above as well as a reagent for conducting a gene amplification reaction. When a PCR is used as a gene amplification reaction using a cDNA as a template, reagents to be used for the amplification reaction include a heat-resistant DNA polymerase, a reaction buffer, nucleotides and other reagents. cDNA can be amplified efficiently, with high fidelity and readily by using such a kit. When a heat-resistant DNA polymerase having a 3'-5' exonuclease activity (e.g., an α-type DNA polymerase from a thermophilic archaebacterium) is used in the cDNA synthesis step, the enzyme can be also used in the PCR step as a DNA polymerase for the amplification reaction as described above.

EXAMPLES

The following examples further illustrate the present invention in detail but are not to be construed to limit the scope thereof.

In Examples below, the activities of the respective enzymes are expressed according to the indications in the instructions attached to the enzymes.

Example 1

Preparation of RNA

Unless otherwise stated, the RNA used in Examples below was prepared from human cultured U-937 cells (ATCC CRL-1593) by using TRIzol reagent (Life Technologies) according to the instructions attached to the reagent. The concentration was then adjusted to 0.66 μg/μl. The purity of the RNA was $OD_{260}/OD_{280}=1.7$.

Example 2

Effect of Combination of BcaBEST DNA Polymerase and Pyrobest DNA Polymerase

The effect of addition of an enzyme having a 3'-5' exonuclease activity during cDNA synthesis was examined using a DNA polymerase derived from *Bacillus caldotenax* lacking its 5'-3' exonuclease activity (BcaBEST DNA polymerase, Takara Shuzo) as a reverse transcriptase and a DNA polymerase derived from Pyrococcus sp. (Pyrobest DNA polymerase, Takara Shuzo) as a 3'-5' exonuclease.

cDNA synthesis reactions were carried out using BcaBEST RNA PCR Kit (Ver. 1.1) (Takara Shuzo). Reaction mixtures each containing the enzyme(s) as described below and an oligo dT primer in a volume of 20 μl were prepared according to the manual attached to the kit. The reaction mixtures were placed in PCR Thermal Cycler PERSONAL (Takara Shuzo) for reverse transcription reactions at 60° C. for 1, 2, 3 or 4 minutes. After reaction for the predetermined time, they were heated at 98° C. for 5 minutes.

Enzyme 1: BcaBEST DNA polymerase 22 U/reaction system

Enzyme 2: BcaBEST DNA polymerase 42 U/reaction system

Enzyme 3: BcaBEST DNA polymerase 22 U+Pyrobest DNA polymerase 0.017 U/reaction system Enzyme 4: BcaBEST DNA polymerase 42 U+Pyrobest DNA polymerase 0.033 U/reaction system PCRs for amplifying a region of 4.4 kb within the mRNA for transferrin receptor were carried out using Pyrobest DNA polymerase and 20 μl each of the reverse transcription reaction mixtures. The PCRs were carried out according to the manual attached to Pyrobest DNA polymerase as follows. Reaction mixtures each containing 20 μl of one of the above-mentioned reverse transcription reaction mixtures, primer 1 for amplifying transferrin receptor (SEQ ID NO: 1) and primer 2 for amplifying transferrin receptor (SEQ ID NO: 2) in a volume of 100 μl were prepared. The reaction mixtures were placed in PCR Thermal Cycler PERSONAL and subjected to PCRs (30 cycles of 94° C. for 30 seconds, 65° C. for 30 seconds and 72° C. for 5 minutes).

After the PCRs, 8 μl each of the resulting reaction mixtures was subjected to electrophoresis on 1% agarose gel using Agarose L03 (Takara Shuzo). The amounts of the PCR products were evaluated by using a fluorescence image analyzer FMBIO II Multi-View (Takara Shuzo) to numerically express the intensity of fluorescence emitted from the agarose gel after electrophoresis and ethidium bromide staining measured. The results for all of the samples converted defining the intensity of fluorescence from the RT-PCR amplification product obtained for the combination of the enzyme 1 and the reverse transcription reaction time of 3 minutes as 1.00 are shown in Table 1.

TABLE 1

| Reaction time | 1 minute | 2 minutes | 3 minutes | 4 minutes |
|---|---|---|---|---|
| Enzyme 1 | n.d. | n.d. | 1.00 | 1.27 |
| Enzyme 2 | n.d. | 1.03 | 2.05 | 2.05 |
| Enzyme 3 | n.d. | n.d. | 1.02 | 1.53 |
| Enzyme 4 | n.d. | 2.31 | 2.88 | 3.19 | n.d.: not detectable.

When 22 U or 42 U of BcaBEST DNA polymerase was used, the efficiency of cDNA synthesis was increased by the addition of Pyrobest DNA polymerase which has a 3'-5' exonuclease activity (Table 1, Enzyme 3 or 4). The increase in efficiency was particularly remarkable when 42 U of BcaBEST DNA polymerase was used (Table 1, Enzyme 4).

These results show that the efficiency of cDNA synthesis is increased by the addition of an enzyme having a 3'-5' exonuclease activity during a reverse transcription reaction and that use of a large amount of an enzyme having a reverse transcription activity further increases the efficiency.

As a control experiment, cDNA was synthesized using Titan RT-PCR Kit from Boehringer. This kit contains AMV-RTase as an enzyme having a reverse transcription activity and Pwo DNA polymerase from *Pyrococcus woesii* as an enzyme having a 3'-5' exonuclease activity.

A cDNA synthesis reaction was carried out at 50° C. for 30 minutes according to the manual attached to the kit. After heating at 94° C. for 2 minutes according to the manual, a PCR for amplifying a region of 4.4 kb within the mRNA for transferrin receptor was carried out using Taq DNA polymerase/Pwo DNA polymerase according to the manual attached to the kit as follows: 10 cycles of 94° C. for 3 seconds, 55° C. for 30 seconds and 68° C. for 4 minutes; 94° C. for 30 seconds, 55° C. for 30 seconds and 68° C. for 4 minutes and 5 seconds (the 11th cycle); 94° C. for 30 seconds, 55° C. for 30 seconds and 68° C. for 4 minutes and 10 seconds (the 12th cycle); 94° C. for 30 seconds, 55° C. for 30 seconds and 68° C. for 4 minutes and 15 seconds (the 13th cycle); to the 25th cycle while prolonging the time of extension step by 5 seconds per cycle.

The RT-PCR product was subjected to electrophoresis on 1% agarose gel. The 4.4-kb amplification product of interest was not detected although the reverse transcription reaction was carried out for 30 minutes.

Example 3

Effect of Combination of BcaBEST DNA Polymerase and Deep Vent DNA Polymerase

The effect of the use of Deep Vent DNA polymerase from *Pyrococcus* sp. GB-D (New England Biolabs) as an enzyme having a 3'-5' exonuclease activity was examined.

Experiments were carried out as described in Example 2 using the following enzyme(s).

Enzyme 1: BcaBEST DNA polymerase 42 U/reaction system
Enzyme 2: BcaBEST DNA polymerase 42 U+Deep Vent DNA polymerase 0.033 U/reaction system
Enzyme 3: BcaBEST DNA polymerase 42 U+Deep Vent DNA polymerase 0.067 U/reaction system The results are shown in Table 2 (defining the result obtained for the combination of the enzyme 1 and the reverse transcription reaction time of 2 minutes as 1.00).

TABLE 2

| Reaction time | 1 minute | 2 minutes | 3 minutes | 4 minutes |
|---|---|---|---|---|
| Enzyme 1 | n.d. | 1.0 | 2.4 | 2.4 |
| Enzyme 2 | n.d. | 1.5 | 4.7 | 7.6 |
| Enzyme 3 | n.d. | 2.3 | 5.0 | 8.9 | n.d.: not detectable.

These results show that the efficiency of cDNA synthesis is increased by using Deep Vent DNA polymerase in place of Pyrobest DNA polymerase as an enzyme having a 3'-5' exonuclease activity.

Example 4

Effect of Combination of Bst DNA Polymerase, Large Fragment and Pyrobest DNA Polymerase The effect of the use of a DNA polymerase derived from *Bacillus stearothermophilus* lacking its 5'-3' exonuclease activity (Bst DNA polymerase, Large fragment, New England Biolabs) as an enzyme having a reverse transcription activity was examined.

Reverse transcription reactions were conducted as described in Example 2 using the following enzyme(s) except that the reverse transcription reaction was carried out for 10 minutes.

Enzyme 1: Bst DNA polymerase, Large fragment 8 U/reaction system
Enzyme 2: Bst DNA polymerase, Large fragment 8 U+Pyrobest DNA polymerase 0.01 U/reaction system
Enzyme 3: Bst DNA polymerase, Large fragment 8 U+Pyrobest DNA polymerase 0.005 U/reaction system
Enzyme 4: Bst DNA polymerase, Large fragment 8 U+Pyrobest DNA polymerase 0.0033 U/reaction system PCRs for amplifying a region of 2.4 kb within the mRNA for transferrin receptor were carried out. The PCRs were carried out as described in Example 2 except that primer 2 for amplifying transferrin receptor (SEQ ID NO: 2) and primer 3 for amplifying transferrin receptor (SEQ ID NO: 3) were used as primers under the following reaction conditions: 30 cycles of 94° C. for 30 seconds, 65° C. for 30 seconds and 72° C. for 3 minutes. The results are shown in Table 3 (defining the result obtained for the enzyme 1 as 1.00).

TABLE 3

| Enzyme 1 | 1.00 |
|---|---|
| Enzyme 2 | 1.61 |
| Enzyme 3 | 1.67 |
| Enzyme 4 | 1.92 |

These results show that the efficiency of cDNA synthesis is increased by the addition of an enzyme having a 3'-5' exonuclease activity when Bst DNA polymerase, Large fragment was used for a reverse transcription reaction as an enzyme having a reverse transcription activity in place of BcaBEST DNA polymerase.

Example 5

Effect of 3'-5' Exonuclease Activity on fidelity during cDNA synthesis

The effect of a 3'-5' exonuclease activity on the fidelity during cDNA synthesis was examined using BcaBEST DNA polymerase as an enzyme having a reverse transcription activity and Pyrobest DNA polymerase as an enzyme having a 3'-5' exonuclease activity according to a modification of the method of J. Cline et al. (J. Cline et al., Nucleic Acids Research, 24:3546–3551 (1996)).

lacIOZα RNA, which was synthesized using SP6 RNA polymerase (Takara Shuzo) as follows, was used as a template RNA for cDNA synthesis.

lacIOZα is a part of *E. coli* lactose operon and contains the repressor region (I), the operator region (O) and the lacZα factor region (Z).

An amplified fragment for the lacIOZα region was obtained by PCR using *E. coli* genomic DNA as a template as well as lacIOZα-F primer (SEQ ID NO: 4) and lacIOZα-R primer (SEQ ID NO: 5). The resulting amplified fragment (about 1.9 kb) was cloned into pSCREEN-T™-1 T-Vector (Novagene), a plasmid having SP6 promoter, by TA cloning to obtain a plasmid in which the lacIOZα region was linked downstream from the SP6 promoter. An RNA was synthesized from the SP6 promoter region using a linear DNA obtained by digesting the plasmid with a restriction enzyme XhoI (Takara Shuzo) as a template with Competitive RNA Transcription Kit (Takara Shuzo) and SP6 RNA polymerase as follows.

A reaction mixture containing 200 ng of the linear lacIOZα-pSCREEN-T DNA in a volume of 50 µl was prepared according to the manual attached to Competitive RNA Transcription Kit. The reaction mixture was incubated at 37° C. for 2 hours to synthesize an RNA. After reaction, 10 U of DNaseI (Takara Shuzo) was added thereto. The mixture was allowed to stand at 37° C. for 1 hour to degrade the DNA. The mixture was then subjected to phenol/chlororform treatment followed by ethanol precipitation to purify the synthesized RNA. The thus obtained lacIOZα RNA of 1991 bases, which contains the SP6 promoter, the repressor region (I), the operator region (O) and the lacZα factor region (Z), was used as a template to carry out the following experiments.

Reaction mixtures each containing 450 ng of the lacIOZα RNA, 20 pmol of the lacIOZα-R primer and the enzyme(s) as described below in a volume of 20 µl were prepared according to the manual attached to BcaBEST RNA PCR Kit. The reaction mixtures were placed in PCR Thermal Cycler PERSONAL (Takara Shuzo), and incubated at 65° C. for 1 minute and then 30° C. for 1 minute. The temperature was raised from 30° C. to 65° C. in 15 minutes. The mixtures were then incubated at 65° C. for 15 minutes for reverse transcription reactions, and finally heated at 98° C. for 5 minutes.

Enzyme 1: BcaBEST DNA polymerase 42 U/reaction system

Enzyme 2: BcaBEST DNA polymerase 42 U+Pyrobest DNA polymerase 0.033 U/reaction system PCRs for amplifying a 1.9-kb region of lacIOZα were carried out using Pyrobest DNA polymerase and 2.5 µl each of the reverse transcription reaction mixtures. The PCRs were carried out according to the manual attached to Pyrobest DNA polymerase as follows. Reaction mixtures each containing 2.5 µl of one of the above-mentioned reverse transcription reaction mixtures, lacIOZα-F primer and lacIOZα-R primer in a volume of 100 µl were prepared. The reaction mixtures were placed in PCR Thermal Cycler PERSONAL and subjected to PCRs (28 cycles of 94° C. for 30 seconds, 68° C. for 2 minutes).

After the PCRs, the resulting reaction mixtures were subjected to phenol/chloroform treatment followed by ethanol precipitation to purify the amplification products. After the amplification products were treated with a restriction enzyme EcoRI (Takara Shuzo), the whole mixtures were subjected to agarose gel electrophoresis. The bands of the EcoRI-treated fragments were excised after electrophoresis, and the EcoRI-treated fragments were recovered using EasyTrap (Takara Shuzo). Each of the thus obtained EcoRI-treated fragments was ligated with λgt10 EcoRI Arms (Takara Shuzo) using Ligation Kit ver.2 (Takara Shuzo). Each of the ligation mixtures was then subjected to in vitro packaging using Gigapack III gold packaging extract (Stratagene).

100 µl each of serial dilutions of the thus obtained packaging mixtures was added to 100 µl of a culture of *E. coli* DH5α (lacZΔM15) (OD600=1). The mixtures were allowed to stand at 37° C. for 15 minutes. The whole mixtures were added to 0.7% LB soft agar containing X-gal (1 mg/ml) and IPTG (1.5 mM) (IPTG (+)) or 0.7% LB soft agar containing X-gal but not containing IPTG (IPTG (−)), mixed, and overlaid onto LB plates. The plates were incubated at 37° C. overnight. The number of the formed plaques was counted.

If there is no mutation in lacI within the lacIOZ region, β-galactosidase is not expressed in the absence of IPTG due to the action of the repressor encoded by the lacI, resulting in white plaques. β-galactosidase is expressed in the presence of IPTG, resulting in blue plaques. On the other hand, if a mutation is introduced into lacI within the lacIOZ region, β-galactosidase is expressed even in the absence of IPTG due to the inactivation of the repressor encoded by the lacI. As a result, blue plaques are formed on the IPTG (+) and IPTG (−) plates.

|  | IPTG (+) | IPTG (−) |
|---|---|---|
| Without mutation | blue | white |
| With mutation | blue | blue |

Accordingly, blue plaques formed on an IPTG (−) plate indicate mutated clones. The mutation frequency (mf) can be determined by dividing the number of blue plaques formed on an IPTG (−) plate by the number of blue plaques formed on an IPTG (+) plate as shown in the following equation.

$$mf = \frac{\text{Number of blue plaques on } IPTG(-) \text{ plate}}{\text{Number of blue plaques on } IPTG(+) \text{ plate}}$$

mf: mutation frequency

The results are shown in Table 4.

TABLE 4

|  | Number of blue plaques on IPTG (−) plate | Number of blue plaques on IPTG (+) plate | Mutation frequency (mf) |
|---|---|---|---|
| Enzyme 1 | 24 | 105 | 0.229 |
| Enzyme 2 | 27 | 203 | 0.133 |

When the reverse transcription reaction was carried out in the presence of BcaBEST DNA polymerase alone, the mutation frequency (mf) was 0.229. On the other hand, when the reverse transcription reaction was carried out in the presence of BcaBEST DNA polymerase and Pyrobest DNA polymerase, the mutation frequency (mf) was 0.133, indicating that the fidelity was about 2-fold higher than that observed in the absence of Pyrobest DNA polymerase.

These results demonstrates that the presence of an enzyme having a 3'-5' exonuclease activity during a reverse transcription reaction increases not only the efficiency of cDNA synthesis but also the fidelity.

INDUSTRIAL APPLICABILITY

The present invention is a method that can be used to synthesize a cDNA with high efficiency of reaction and high fidelity. By combining the method with related techniques such as cloning techniques and PCR techniques, it is possible to prepare a cDNA library or to conduct an RT-PCR more efficiently and more accurately as compared with conventional methods, resulting in improvement in mRNA analysis methods.

Sequence Listing Free Text

SEQ ID NO: 1: Designed oligonucleotide primer designated as Primer 1 to amplify transferrin receptor mRNA.

SEQ ID NO: 2: Designed oligonucleotide primer designated as Primer 2 to amplify transferrin receptor mRNA.

SEQ ID NO: 3: Designed oligonucleotide primer designated as Primer 3 to amplify transferrin receptor mRNA.

SEQ ID NO: 4: Designed oligonucleotide primer designated as lacIOZα-F to amplify lacIOZα region of E. coli.

SEQ ID NO: 5: Designed oligonucleotide primer designated as lacIOZα-R to amplify lacIOZα region of E. coli.

What is claimed is:

1. A kit for cDNA synthesis, which contains a mixture of a DNA polymerase from a thermophilic bacterium of the genus *Bacillus* and another DNA polymerase having a 3'-5' exonuclease activity, wherein said DNA polymerase from a thermophilic bacterium of the genus *Bacillus* has a reverse transcription activity and a 3'-5' exonuclease activity.

2. The kit according to claim 1, wherein the DNA polymerase from a thermophilic bacterium of the genus *Bacillus* is a DNA polymerase from *Bacillus caldotenax* or a DNA polymerase from *Bacillus stearothermophilus*.

3. The kit according to claim 1, wherein the DNA polymerase having a 3'-5' exonuclease activity is an α-type DNA polymerase from an archaebacterium.

4. A kit for amplifying a cDNA by conducting a gene amplification reaction using a cDNA, synthesized according to a method in which a reverse transcription reaction is conducted in the presence of a DNA polymerase from a thermophilic bacterium of the genus *Bacillus* and another DNA polymerase having a 3'-5' exonuclease activity, as a template, wherein said kit contains a mixture of a DNA polymerase from a thermophilic bacterium of the genus *Bacillus* and another DNA polymerase having a 3'-5' exonuclease activity as well as a reagent for the gene amplification reaction, wherein said DNA polymerase from a thermophilic bacterium of the genus *Bacillus* has a reverse transcription activity and a 3'-5' exonuclease activity.

5. The kit according to claim 4, wherein the gene amplification reaction is PCR.

6. The kit according to claim 5, which contains a DNA polymerase for PCR as the reagent for the gene amplification reaction.

7. The kit according to claim 6, wherein the DNA polymerase having a 3'-5' exonuclease activity in the mixture serves as the DNA polymerase for the PCR.

8. The kit according to claim 7, wherein the DNA polymerase having a 3'-5' exonuclease activity is an α-type DNA polymerase from an archaebacterium.

* * * * *